United States Patent [19]

Buchecker et al.

[11] Patent Number: 5,082,589
[45] Date of Patent: Jan. 21, 1992

[54] LIQUID CRYSTALLINE ESTERS

[75] Inventors: Richard Buchecker, Zurich, Switzerland; Hans-Jurgen Fromm, Lorrach, Fed. Rep. of Germany; Stephen Kelly, Kaiseraugst; Martin Schadt, Seltisberg, both of Switzerland

[73] Assignee: Hoffmann-La Roche Inc., Nutley, N.J.

[21] Appl. No.: 485,710

[22] Filed: Feb. 27, 1990

Related U.S. Application Data

[62] Division of Ser. No. 283,655, Dec. 13, 1988, Pat. No. 4,925,278, which is a division of Ser. No. 52,659, May 20, 1987, Pat. No. 4,830,470.

[51] Int. Cl.$^5$ .................. C09K 19/30; C09K 19/52; C07C 69/76
[52] U.S. Cl. .................. 252/299.63; 252/299.01; 560/65; 560/73; 560/128; 359/103; 359/104
[58] Field of Search .................. 350/350 S, 350 R; 282/299.5, 299.6, 299.61, 299.62, 299.63, 299.64, 299.65, 299.66, 299.67; 560/65, 73, 128

[56] References Cited

U.S. PATENT DOCUMENTS

| | | | |
|---|---|---|---|
| 4,173,545 | 11/1979 | Beguin et al. | 252/299.64 |
| 4,212,762 | 7/1980 | Dubois et al. | 252/299.64 |
| 4,279,770 | 7/1981 | Inukai et al. | 252/299.63 |
| 4,293,434 | 10/1981 | Deutscher et al. | 252/299.634 |
| 4,299,315 | 10/1982 | Krause et al. | 252/299.63 |
| 4,368,135 | 1/1983 | Osman | 252/299.63 |
| 4,480,117 | 10/1984 | Takatsu et al. | 252/299.63 |
| 4,510,069 | 4/1985 | Eidenschink et al. | 252/299.63 |
| 4,519,936 | 5/1985 | Demus et al. | 252/299.63 |
| 4,526,704 | 7/1985 | Petrzilka et al. | 252/299.63 |
| 4,551,264 | 11/1985 | Eidenschink et al. | 252/299.63 |
| 4,564,694 | 1/1986 | Hirai et al. | 252/299.63 |
| 4,565,425 | 1/1986 | Petrzilka et al. | 252/299.5 |
| 4,584,120 | 4/1986 | Fujii et al. | 252/299.63 |
| 4,602,851 | 7/1986 | Jenner et al. | 350/350 R |
| 4,610,805 | 9/1986 | Schellenberger et al. | 252/299.63 |
| 4,621,901 | 11/1986 | Petrzilka et al. | 350/350 R |
| 4,629,581 | 12/1986 | Petrzilka et al. | 252/299.63 |
| 4,642,199 | 2/1987 | Sugimori | 252/299.63 |
| 4,670,182 | 6/1987 | Fijita et al. | 252/299.63 |
| 4,676,604 | 6/1987 | Petrzilka | 252/299.63 |
| 4,709,030 | 11/1987 | Petrzilka et al. | 252/299.63 |
| 4,729,847 | 3/1988 | Miyazawa et al. | 252/299.64 |
| 4,780,240 | 10/1988 | Emoto et al. | 252/299.6 |

FOREIGN PATENT DOCUMENTS

| | | |
|---|---|---|
| 0087102 | 2/1982 | European Pat. Off. |
| 0164814 | 12/1985 | European Pat. Off. |
| 2736424 | 2/1978 | Fed. Rep. of Germany |
| 2736772 | 4/1978 | Fed. Rep. of Germany |
| 2752975 | 8/1978 | Fed. Rep. of Germany |
| 57-149250 | 9/1982 | Japan |
| 58-13545 | 1/1983 | Japan |
| 58-13546 | 1/1983 | Japan |
| 58-203943 | 1/1983 | Japan |
| 59-167542 | 9/1984 | Japan |
| 59-170030 | 9/1984 | Japan |
| 61-10544 | 1/1986 | Japan |
| 63-188653 | 10/1986 | Japan |
| 61-229842 | 10/1986 | Japan |
| 61-243037 | 10/1986 | Japan |
| 2010272 | 6/1979 | United Kingdom |
| 87/05017 | of 0000 | World Int. Prop. O. |

OTHER PUBLICATIONS

Demus et al., Flussige Kristalle in Tabellen, II, pp. 43, 52-53, 63 (1984).
Gray et al., Liquid Crystals & Plastic Crystals, vol. 1, pp. 142-143 (1974).
Mol. Cryst. Liq. Cryst. vol. 42, pp. 139-152 (1977).
Mol. Cryst. Liq. Cryst. vol. 47, pp. 193-200 (1978).
Mol. Cryst. Liq. Cryst., vol. 53, pp. 29-41 (1979).
Mol. Cryst. Liq. Cryst., vol. 53, pp. 43-54 (1979).
Mol. Cryst. Liq. Cryst., vol. 114, pp. 237-247 (1984).
Liq. Cryst. Ordered Fluids, vol. 4, pp. 1-32 (1984).
Science, vol. 231, pp. 350-355 (1986).
16 Freiburger Arbeitstagung Flussigkristalle, Mar. 16-21, 1986.
Liquid Crystals, 5(1), 171 (1989).
Liquid Crystals, 5(4), 179 (1989).
Ferroelectrics, 85, 385 (1988).
Helvetica Chimica Acta 71, 451 (1988).
Helvetica Chimica Acta 71, 461 (1988).
Helvetica Chimica Acta, 72, 594 (1989).

*Primary Examiner*—John S. Maples
*Assistant Examiner*—Shean C. Wu
*Attorney, Agent, or Firm*—George M. Gould; George W. Johnston; Alan P. Kass

[57] ABSTRACT

Compounds of the formula

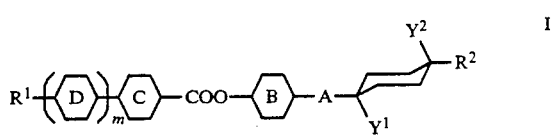

wherein m represents is the number of 0 to 1; A is a single convalent bond, —$CH_2$—$CH_2$—, —$OCH_2$—, —COO— or —OOC—; rings B, C and D are 1,4-phenylene optionally substituted with cyano, halogen or lower alkyl; $Y^1$ and $Y^2$ are hydrogen or one of them also is cyano; and $R^1$ and $R^2$ each represents $C_1$-$C_{18}$-alkyl or $C_2$-$C_{18}$ alkenyl, either of which is optionally halogen-substituted, in which one $CH_2$ group or two non-adjacent $CH_2$ groups is/are optionally replaced by oxygen: with the provisos that at least one of $R^1$ and $R^2$ has a chiral carbon atom or $R^1$ is straight-chain $C_{4-18}$-alkoxy and $R^2$ is straight $C_{3-18}$-alkyl or a C—C double bond or both when A is —COO— and at least one of $R^1$ and $R^2$ has a C—C double bond when A is a single covalent bond, their preparation, liquid crystalline mixtures containing these compounds and their use for electro-optical purposes are described.

5 Claims, No Drawings

LIQUID CRYSTALLINE ESTERS

This is a division of application Ser. No. 07/283,655, filed Dec. 13, 1988, now U.S. Pat. No. 4,925,278 which is a division of Ser. No. 07/052,659, filed May 20, 1987, now U.S. Pat. No. 4,830,470.

BACKGROUND OF THE INVENTION

1. Field of the Invention

The present invention relates to liquid crystalline compounds and mixtures as well as electro-optical devices.

2. Description of the Art

Liquid crystals are used primarily as dielectrics in indicating devices, since the optical properties of such substances can be influenced by an applied voltage. Electro-optical devices based on liquid crystals are well-known to the person skilled in the art and can be based on various effects such as, for example, dynamic scattering, the deformation of aligned phases (DAP cells), the Schadt-Helfrich effect (TN cells, i.e., twisted-nematic, and STN cells i.e., super twisted-nematic), the quest/host effect (guest/host cells), a choloesteric-nematic phase transition (phase-change cells) or the SBE effect (super birefringence effect).

Cholesteric liquid crystals are used, for example, in the above-mentioned phase-change cells. Further, cholesteric additives or other chiral substances with suitable choice of the concentration can also be used to improve the electro-optical properties of liquid crystals for TN cell indicators. Nematic liquid crystal components can be used in all of the aforementioned applications.

The aforementioned indicating devices generally have response times in the order of several milliseconds or more. In order to improve the response times of indicating devices, liquid crystals with ferroelectric properties have recently also been used. In this application there are used chiral smectic phases, for example, smectic C, F or I phases, mainly smectic C phases. Hitherto, however, relatively few of such liquid crystals have become known and their stability is often inadequate.

In order to be suitable for use in indicating devices liquid crystals should have a good chemical and thermal stability and a good stability towards electrical fields and electromagnetic radiation. Further, they should be colorless and have low viscosities and should give short response times and a high contrast in indicating devices. Furthermore, the liquid crystals should have a suitable mesophase, for example, a cholesteric or a suitable chiral smectic phase, at the usual operating temperatures. Because liquid crystals are usually employed in mixtures, it is important that the components have a good miscibility with one another. Other properties such as, for example, the threshold potential, the dielectric anisotropy and the optical anisotropy, must fulfil different conditions depending on the type of cell used. Liquid crystals with ferroelectric properties preferably have a negative dielectric anisotropy or a small absolute value of the dielectric anisotropies.

SUMMARY

The present invention provides tricyclic and tetracyclic esters of the formula

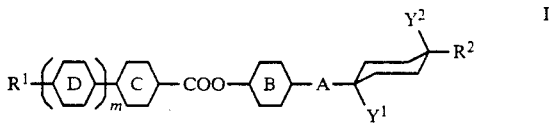

wherein m is for the number 0 or 1; A is a single covalent bond, $-CH_2-CH_2-$, $-OCH_2-$, $-COO-$ or $-OOC-$; rings B, C and D are 1,4-phenylene unsubstituted or substituted with cyano, halogen or lower alkyl; $Y^1$ and $Y^2$ are hydrogen or one of these substituents $Y^1$ and $Y^2$ also is cyano; and $R^1$ and $R^2$ each individually represents $C_1-C_{18}$ alkyl or $C_2-C_{18}$ alkenyl, either of which is optionally halogen-substituted, in which one $CH_2$ group or two non-adjacent $CH_2$ groups is/are optionally replaced by oxygen; with the provisos that at least one of $R^1$ and $R^2$ has a chiral carbon atom or $R^1$ is straight-chain $C_{4-18}$-alkoxy and $R^2$ is straight $C_{3-18}$-alkyl or a C—C double bond or both when A is $-COO-$ and at least one of $R^1$ and $R^2$ has a C—C double bond when A stands for a single covalent bond.

DETAILED DESCRIPTION OF THE PRESENT INVENTION

The compounds in accordance with the invention are suitable components for ferroelectric liquid crystals and themselves have, for the most part, a chiral smectic phase. They are, however, also suitable for cholesteric or nematic mixtures. They are optically active or optically inactive and have the requisite properties referred to above.

The above term "halogen" embraces fluorine, chlorine or bromine.

The term "lower alkyl" embraces alkyl groups with 1-5 carbon atoms such as methyl, ethyl, propyl and isopropyl, preferably methyl.

The terminology "1,4-phenylene optionally substituted with cyano, halogen or lower alkyl" embraces groups such as 1,4-phenylene, 2-cyano-1,4-phenylene, 2,3-dicyano-1,4-phenylene, 2-fluoro-1,4-phenylene, 2,3-difluoro-1,4-phenylene, 2-chloro-1,4-phenylene, 2-bromo-1,4-phenylene, 2-methyl-1,4-phenylene, and the like. The compound 1,4-phenylene is generally preferred. However, the transition temperatures, solubility, dielectric anisotropy, and the like, can be modified and higher ordered phases can be suppressed by using substituted groups.

The terminology "alkyl or alkenyl in which optionally one $CH_2$ group or two non-adjacent $CH_2$ groups is/are replaced by oxygen" embraces straight-chain and branched groups such as alkyl, alkoxy, alkoxyalkyl, alkoxyalkoxy, alkenyl, alkenyloxy, alkoxyalkenyl, alkenyloxyalkyl, alkoxyalkenyloxy, and the like. Corresponding halogen-substituted groups are, for example, halogenoalkyl, halogenoalkoxy, halogenoalkenyl, halogenoalkenyloxy, and the like.

Compounds of formula I in which $Y^1$ or $Y^2$ signifies cyano have a negative anisotropy of the dielectric constants. In general, however, $Y^1$ and $Y^2$ preferably are hydrogen. In many instances, C—C double bonds in $R^1$ or $R^2$, or both, lead to an improvement of the chiral smectic properties.

A preferred group of compounds in accordance with the invention comprises those in which $Y^1$ and $Y^2$ are hydrogen and ring C and optionally present ring D are 1,4-phenylene. Ring B preferably denotes 1,4-phenylene, 2-cyano-1,4-phenylene, 2,3-dicyano-1,4-phenylene, 2-halogeno-1,4-phenylene or 2,3-dihalogeno-1,4-phenylene.

A further group of preferred compounds of formula I comprises those in which A is —CH₂CH₂—, —OCH₂— or —OOC—, especially —CH₂CH₂— or —OCH₂—.

In formula I, above, m preferably is zero.

A further preferred aspect is concerned with optically active compounds of formula I which have a chiral carbon atom in R¹ and/or R², or both.

Preferred groups R¹ or R² having chiral carbon atoms are those groups of the general formulae

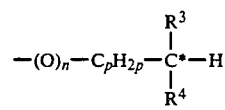

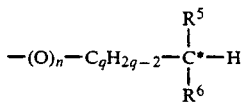

wherein n, p and q are whole numbers and n is zero or 1, p is zero to 6 and q is 2 to 6; R³ is alkyl and R⁴ is halogen, alkoxy, alkenyl, alkenyloxy or alkyl different from R³; or R³ is alkenyl and R⁴ is alkoxy; R⁵ denotes alkyl; R⁶ denotes halogen, alkoxy or alkyl different from R⁵; and C* is the chiral carbon atom.

Groups of formula II in which R³ is methyl and R⁴ is alkyl different from methyl, preferably ethyl, are especially preferred.

In the case of optically active compounds of formula I, R¹ preferably has a chiral carbon atom. Those compounds of formula I in which R¹ is a group of formula II or III are, therefore, especially preferred.

Alkyl, alkenyl, alkoxyalkenyl and alkenyloxyalkyl are preferred for R². When R¹ has a chiral carbon atom, R² preferably is a straight-chain residue.

In general, particularly preferred are those compounds of formula I in which R¹ is a chiral or achiral alkoxy or alkenyloxy group and R² is a chiral or achiral alkyl or alkenyl group. R² is preferably achiral.

A double bond optionally present in R¹ or R², or both, is preferably situated in position 1, 3 or 4 (including oxygen atoms which may be present) or in the terminal position of the side-chain R¹ or R², especially in position 4. Especially preferred unsaturated groups are, therefore, groups such as 1E-alkenyl, 3E-alkenyl, 4-alkenyl, 2E-alkenyloxy, 3-alkenyloxy, alkoxy-3E-alkenyl, alkoxy-4-alkenyl, alkoxy-3-alkenyloxy, 5-hexenyl, 4-pentenyloxy, 6-heptenyl, 5-hexenyloxy, 7-octenyl, 6-hep-tenyloxy, 8-nonenyl, 7-octenyloxy, 9-decenyl, 8-nonenyloxy, and the like.

The groups R¹ and R² conveniently have a maximum of 18 carbon atoms in each case. The group or groups with a chiral carbon atom preferably have from 4 to 18, particularly 4 to 15, carbon atoms. An optionally present group R¹ or R² without a chiral carbon atom preferably has a maximum of 12, particularly a maximum of 7, carbon atoms. For chiral smectic applications there are, however, generally preferred compounds of formula I which have in R¹ and R² together at least 7, especially at least 10, carbon atoms.

The compounds of formula I can be prepared in accordance with the invention by a) esterifying a compound of the general formula

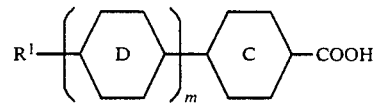

and a compound of the general formula

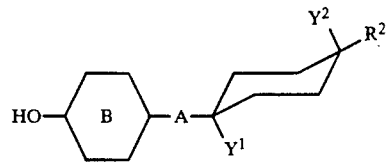

wherein A, R¹, R², Y¹, Y², m and rings B, C and D are as defined above, or reactive derivatives of these compounds and, if desired, reacting a compound of formula I in which ring B, C or D is 1,4-phenylene substituted with chlorine or bromine, with copper(I) cyanide, sodium cyanide or potassium cyanide, or b) for the manufacture of compounds of formula I in which A is an ester group —COO— or —OOC—, esterifying a compound of the general formula

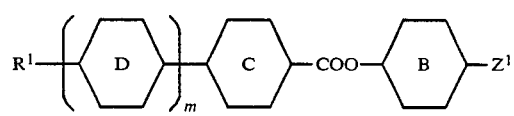

and a compound of the general formula

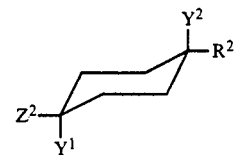

wherein one of Z¹ and Z² denotes the carboxyl group and the other denotes the hydroxy group and R¹, R², Y¹, Y², m and rings B, C and D are as defined above, or reactive derivatives of these compounds and, if desired, reacting a compound of formula I obtained in which ring B, C or D is 1,4-phenylene substituted with chlorine or bromine, with copper(I) cyanide, sodium cyanide or potassium cyanide.

The reaction of the compounds of formulae IV and V or of the compounds of formulae VI and VII can be carried out in a known manner by esterifying the carboxylic acid or a reactive derivative thereof (e.g., acid chloride, bromide or anhydride) with the hydroxy compound or a suitable salt (e.g., the sodium salt). A preferred method comprises reacting the acid chloride (which is obtainable from the carboxylic acid, such as by heating with thionyl chloride) with the hydroxy compound. This reaction is conveniently carried out in an inert organic solvent, for example, one of which is diethyl ether, tetrahydrofuran, dimethylformamide, benzene, toluene, cyclohexane, carbon tetrachloride, and the like. In order to bind the hydrogen chloride liberated during the reaction, an acid-binding agent, for example, a tertiary amine, pyridine, and the like, is conveniently used. The acid-binding agent can also simultaneously serve as the solvent. Further preferred methods comprise reacting the carboxylic acid with the hydroxy compound in the presence of 4-(dimethylamino)pyridine and N,N'-dicyclohexylcarbodiimide or in the presence of oxalyl chloride and dimethylformamide. The temperature and pressure at which the above esterification reactions are carried out are not critical and, in general, are carried out at atmospheric pressure and a temperature between −30° C. and the boiling temperature of the reaction mixture.

The reaction of a compound of formula I in which ring B, C or D is 1,4-phenylene substituted with chlorine or bromine to give the corresponding cyano-substituted compound is conveniently carried out with copper(I) cyanide, sodium cyanide or potassium cyanide, in an inert organic solvent such as ethylene glycol, tetrahydrofuran, dimethylformamide, dimethyl sulphoxide, pyridine or acetonitrile. The temperature and pressure are not critical. Atmospheric pressure and a temperature between room temperature and the boiling temperature of the reaction mixture are conveniently used.

The starting materials of formulae IV–VII are known compounds or analogs of known compounds and can be prepared according to known methods.

The compounds in accordance with the invention can be used in the form of mixtures with one another and/or with other liquid crystal components. They are especially suitable for the manufacture of chiral smectic mixtures, primarily for mixtures with a smectic C phase. However, they can also be used as additives for nematic mixtures (in the case of optically inactive compounds) or cholesteric mixtures. The mixtures in accordance with the invention contain at least 2 components, of which at least one component is a compound of formula I. The amount of compounds of formula I in the mixtures in accordance with the invention can vary over a wide range depending on the use and, for example, from about 1% to 100%. In general, the mixtures in accordance with the invention with a nematic, cholesteric or chiral smectic phase contain about 1–80 wt. %, preferably about 5–50 wt. %, of compounds of formula I. An especially preferred range for chiral smectic mixtures amounts to about 10–70 wt. %, particularly about 30–50 wt. %. When optically active compounds of formula I are used as additives in mixtures for TN cell applications, the amount thereof can also be smaller and can, for example, amount to about 0.2–10 wt. % depending on the pitch and the cell thickness.

The liquid crystal mixtures in accordance with the invention with nematic or cholesteric properties and the mixtures for TN cell indicators preferably contain, in addition to one or more compounds of formula I, one or more of the compounds of the following formulae

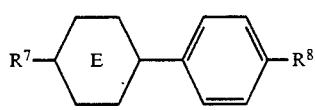  VIII

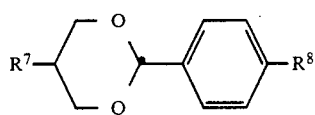  IX

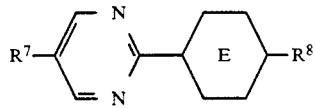  X

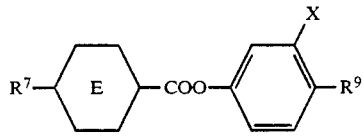  XI

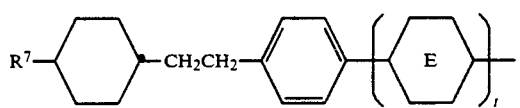  XII

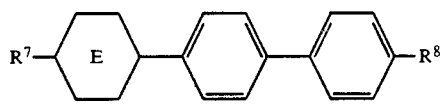  XIII

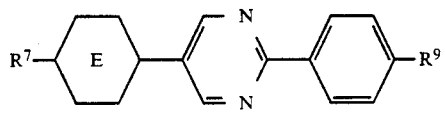  XIV

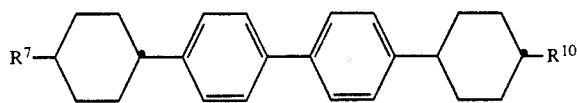  XV

-continued

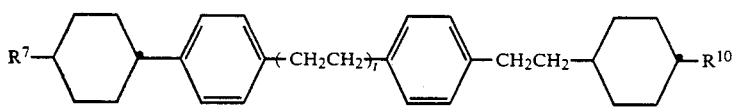

XVI wherein $R^7$, $R^8$, $R^9$ and $R^{10}$ each independently are alkyl, alkoxy, alkenyl or alkenyloxy with a maximum of 7 carbon atoms in each case, or $R^8$ on a benzene ring also can be cyano or —NCS, or $R^9$ on a benzene ring also can be cyano; ring E represents trans-1,4-cyclohexylene or 1,4-phenylene; X denotes hydrogen or fluorine; and t is 0 or 1.

The liquid crystal mixtures in accordance with the invention with chiral smectic phases can contain, in addition to one or more compounds of formula I, usual components for chiral smectic mixtures. They preferably contain one or more compounds of the formulae

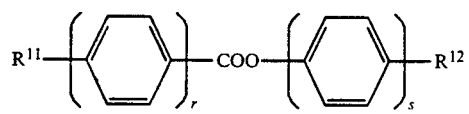

XVII

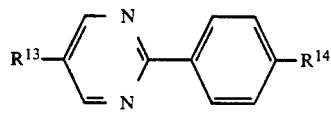

XVIII

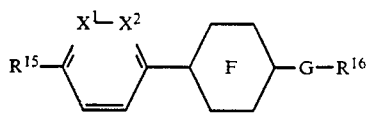

XIX

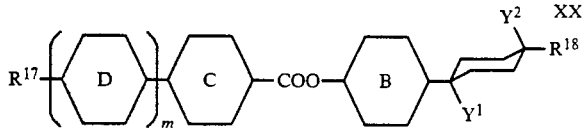

XX wherein $R^{11}$ and $R^{12}$ are alkyl, alkoxy, alkanoyl, alkanoyloxy, alkoxycarbonyl or alkoxycarbonyloxy with up to 18 carbon atoms; r and s are 1 or 2; $R^{13}$ and $R^{14}$ are alkyl or alkoxy with 1 to 18 carbon atoms; $X^1$ is CH and $X^2$ is N, or $X^1$ is N and $X^2$ is CH; G is a single covalent bond, trans-1,4-cyclohexylene, cis-4-cyano-trans-1,4-cyclohexylene or 1,4-phenylene optionally substituted with halogen or methyl; ring F is trans-1,4-cyclohexylene, 1,4-phenylene optionally substituted with halogen or methyl, or, when G is a single covalent bond, also cis-4-cyano-trans-1,4-cyclohexylene; $R^{15}$ and $R^{16}$ each denotes an optionally halogen-substituted alkyl or alkenyl group in which optionally one $CH_2$ group or two non-adjacent $CH_2$ groups is/are replaced by —O—, —COO— and/or —OOC—; m, $Y^1$, $Y^2$ and rings B, C and D have the meanings given in formula I; and $R^{17}$ and $R^{18}$ are $C_1$-$C_{18}$ alkyl in which optionally one $CH_2$ group or two non-adjacent $CH_2$ groups is/are replaced by oxygen.

The chiral smectic mixtures in accordance with the invention can consist of optically inactive compounds. However, they preferably contain one or more optically active compounds in order to produce a spontaneous polarization, i.e., they preferably contain at least one optically active compound of formula I with a chiral carbon atom in $R^1$ and/or $R^2$ and/or at least one optically active additive. Preferred chiral smectic mixtures with at least 2 components are, accordingly, those in which at least one component is an optically active compound of formula I and a second component can be optically active or optically inactive, as well as those in which at least one component is an optically inactive, preferably achiral, compound of formula I and a second component is optically active. The second component is preferably a further compound of formula I or a compound of formulae XVII-XX.

The optically active compounds of formula XX which are laterally-substituted on B, C and/or D and-/or which are axially-substituted on the cyclohexane ring are novel. They can be manufactured in a manner an analogous to the compounds of formula I.

The mixtures in accordance with the invention can also contain dichroic coloring substances, for example, azo, azoxy or anthraquinone coloring substances. The amount of coloring substance is determined by the solubility and the desired color, extinction, and the like, and generally amounts to a maximum of about 10 wt. % in the total mixture.

A practical application of the compound of this invention is in an electro-optical cell, which comprises
 (a) two-plate means;
 (b) a liquid crystal disposed between the plate means and which includes a dielectric of the formula:

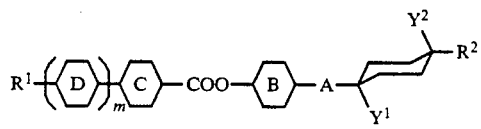

I wherein m is the number 0 or 1; A is a single covalent bond, —$CH_2$—$CH_2$—, —$OCH_2$—, —COO— or —OOC—; rings B, C and D are 1,4-phenylene optionally substituted with cyano, halogen or lower alkyl; $Y^1$ and $Y^2$ are hydrogen or one of these substituents also is cyano; and $R^1$ and $R^2$ each represents $C_1$-$C_{18}$-alkyl or $C_2$-$C_{18}$ alkenyl, either of which is optionally halogen-substituted, in which one $CH_2$ group or two non-adjacent $CH_2$ group is/are optionally replaced by oxygen; with the provisos that at least one of $R^1$ and $R^2$ has a chiral carbon atom and/or a C—C double bond when A is —COO— and at least one of $R^1$ and $R^2$ has a C—C double bond when A is a single covalent bond; and
 (c) a means for applying an electrical potential to said plate means.

The preparation of the mixtures and electro-optical devices of this invention can be effected using known ways.

The preparation of the compounds in accordance with the invention, of the novel compounds of formula XX and of the starting materials as well as mixtures in accordance with the invention are illustrated in greater detail in the following Examples. The phases are denoted by the following symbols: C is crystalline, S is smectic, $S_A$ is smectic A, $S_B$ is smectic B, $S_C$ is smectic C, S*$_C$ is chiral smectic C, Ch is cholesteric, N is nematic and I is isotropic.

EXAMPLE 1

A solution of 2.6 g of boron tribromide in 50 ml of absolute dichloromethane was treated dropwise at 0° C. with a solution of 2.0 g of 2-(trans-4-pentylcyclohexyl)-1-(4-methoxyphenyl)ethane in 50 ml of absolute dichloromethane. The mixture was stirred for 1 hour and then poured into ice-water. The organic phase was separated and the aqueous phase was back-extracted three times with 50 ml of dichloromethane each time. The combined organic phases were washed with 50 ml of 2N sodium carbonate solution and several times with water, dried over magnesium sulphate and concentrated. Recrystallization of the resulting crude product from hexane at 0° C. gave 1.8 g of 4-[2-(trans-4-pentylcyclohexyl)ethyl]phenol of m.p. 102° C.

EXAMPLE 2

A mixture of 5.0 g of (trans-4-heptylcyclohexyl)methyl bromide, 10.0 g of hydroquinone, 10.0 g of anhydrous potassium carbonate and 100 ml of absolute dimethylformamide was heated under reflux overnight. The cooled reaction mixture was subsequently poured into ice-water and extracted three times with 50 ml of diethyl ether each time. The organic phases were washed with 500 ml of water, dried over magnesium sulphate and concentrated. Chromatography of the residue on silica gel with toluene/ethyl acetate (vol. 4:1) gave 1.8 g of 4-[(trans-4-heptylcyclohexyl)methoxy]phenol; m.p. 107°–108° C.

EXAMPLE 3

A finely powdered mixture was prepared from 2.2 g of 2-(trans-4-pentylcyclohexyl)-1-(2,3-dicyano-4-butyloxyphenyl)ethane, 1.4 g of anhydrous aluminium chloride and 0.3 g of sodium chloride and this mixture was heated to 150° C. on an oil-bath for 40 minutes under anhydrous conditions. The cooled mixture was treated with 250 ml of water and extracted three times with 50 ml of dichloromethane each time. The combined organic phases were washed with 250 ml of water, dried over magnesium sulphate and concentrated. Chromatography of the residue on silica gel with toluene/ethyl acetate (vol. 4:1) gave 0.6 g of 2,3-dicyano-4-[2-(trans-4-pentylcyclohexyl)ethyl]phenol; m.p. 100°–102° C.

EXAMPLE 4

A solution of 2.7 g of 4-[2-(trans-4-pentylcyclohexyl)ethyl]phenol in absolute dichloromethane was treated dropwise at 0° C. with a solution of 1.6 g of bromine in 20 ml of absolute dichloromethane. The mixture was stirred for 1 hour and then poured into ice-water. The organic phase was separated and the aqueous phase was back-extracted three times with 50 ml of dichloromethane each time. The combined organic phases were washed with 50 ml of 2N sodium carbonate solution and several times with water, dried over magnesium sulphate and concentrated. Recrystallization of the resulting crude product from hexane at 0° C. gave 3.4 g of 2-bromo-4-[2-(trans-4-pentylcyclohexyl)ethyl]phenol.

EXAMPLE 5

A mixture of 0.25 g of (S)-4-(6-methyloctyloxy)benzoic acid, 5 ml of thionyl chloride (excess) and 20 ml of toluene was heated to boiling for 1 hour. The solvent and excess thionyl chloride were subsequently distilled off and the residue was taken up twice in 25 ml of toluene each time and concentrated each time.

The crude (S)-4-(6-methyloctyloxy)benzoyl chloride obtained was dissolved in 20 ml of toluene and then added dropwise to a solution of 0.26 g of 4-[2-(trans-4-pentylcyclohexyl)ethyl]phenol in 2 ml of pyridine. The reaction mixture was stirred at room temperature overnight, then poured into ice-water and extracted with diethyl ether. The extract was washed four times with 25 ml of 3N hydrochloric acid each time, then washed with 25 ml of 2N sodium carbonate solution and several times with water, dried over magnesium sulphate and concentrated. Chromatography of the residual oil on silica gel with toluene gave 0.2 g of (S)-4-(6-methyloctyloxy)benzoic acid 4-[2-(trans-4-pentylcyclohexyl)ethyl]phenyl ester. The product was recrystallized several times from ethanol until the phase transition temperatures were constant. M.p. (C-S) 58°, transition S-S*$_C$ 58.5° C., transition S*$_C$-Ch 93° C., cl.p. (Ch-I) 140° C.

The following compounds can be prepared in an analogous manner:

(S)-4-(2-Methylbutyloxy)benzoic acid 4-[2-(trans-4-propylcyclohexyl)ethyl]phenyl ester, m.p. (C-Ch) 81° C., cl.p. (Ch-I) 146° C.;

(S)-4-(3-methylpentyloxy)benzoic acid 4-[2-(trans-4-propylcyclohexyl)ethyl]phenyl ester, (S)-4-(4-methylhexyloxy)benzoic acid 4-[2-(trans-4-propylcyclohexyl)ethyl]phenyl ester m.p. (C-Ch) 82° C., cl.p. (Ch-I) 149° C.;

(S)-4-(5-methylheptyloxy)benzoic acid 4-[2-(trans-4-propylcyclohexyl)ethyl]phenyl ester, (S)-4-(6-methyloctyloxy)benzoic acid 4-[2-(trans-4-propylcyclohexyl)ethyl]phenyl ester, m.p. (C-S*$_C$) 73° C., transition S-S*$_C$ 60.5° C., transition S*$_C$-Ch 77° C., cl.p. (Ch-I) 144° C.;

(S)-4-(2-methylbutyloxy)benzoic acid 4-[2-(trans-4-pentylcyclohexyl)ethyl]phenyl ester, m.p. (C-Ch) 74° C., cl.p. (Ch-I) 130° C.;

(S)-4-(3-methylpentyloxy)benzoic acid 4-[2-(trans-4-pentylcyclohexyl)ethyl]phenyl ester, (S)-4-(4-methylhexyloxy)benzoic acid 4-[2-(trans-4-pentylcyclohexyl)ethyl]phenyl ester, m.p. (C-Ch) 66° C., cl.p. (Ch-I) 137° C.;

(S)-4-(5-methylheptyloxy)benzoic acid 4-[2-(trans-4-pentylcyclohexyl)ethyl]phenyl ester, (S)-4-(2-methylbutyloxy)benzoic acid 4-[2-(trans-4-heptylcyclohexyl)ethyl]phenyl ester, m.p. (C-Ch) 66° C., cl.p. (Ch-I) 131° C.;

(S)-4-(4-methylhexyloxy)benzoic acid 4-[2-(trans-4-heptylcyclohexyl)ethyl]phenyl ester, m.p. (C-S) −6° C., transition S-S 61.5° C., transition S-S*$_C$ 69.5° C., transition S*$_C$-Ch 75° C., cl.p. (Ch-I) 135.5° C.;

(S)-4-(6-methyloctyloxy)benzoic acid 4-[2-(trans-4-heptylcyclohexyl)ethyl]phenyl ester, m.p. (C-S) 42° C., transition S-S 44° C., transition S-S*$_C$ 68.5° C., transition S*$_C$-Ch 102.5° C., cl.p. (Ch-I) 135.5° C.;

(S)-4'-(2-methylbutyl)-4-biphenylcarboxylic acid 4-[2-(trans-4-pentylcyclohexyl)ethyl]phenyl ester, m.p. (C-S$_B$) 96° C., transition S$_B$-S*$_C$ 102° C., transition S*$_C$-Ch 104° C., cl.p. (Ch-I) 238.5° C.;

(S)-4'-(4-methylhexyl)-4-biphenylcarboxylic acid 4-[2-(trans-4-pentylcyclohexyl)ethyl]phenyl ester, (S)-4'-(2-methylbutyloxy)-4-biphenylcarboxylic acid 4-[2-(trans-4-pentylcyclohexyl)ethyl]phenyl ester, m.p. (C-S*$_C$) 128° C., transition S*$_C$-Ch 130° C., cl.p. (Ch-I) 247° C.;

(S)-4'-(4-methylhexyloxy)-4-biphenylcarboxylic acid 4-[2-(trans-4-pentylcyclohexyl)ethyl]phenyl ester, (S)-4-(2-methylbutyloxy)benzoic acid 4-[(trans-4-propylcyclohexyl)methoxy]phenyl ester, m.p. (C-Ch) 91.5° C., cl.p. (Ch-I) 143.5° C.;

(S)-4-(4-methylhexyloxy)benzoic acid 4-[(trans-4-propylcyclohexyl)methoxy]phenyl ester, m.p. (C-Ch) 74° C., cl.p. (Ch-I) 148° C.;

(S)-4-(6-methyloctyloxy)benzoic acid 4-[(trans-4-propylcyclohexyl)methoxy]phenyl ester, m.p. (C-S*$_C$) 83° C., transition S-S*$_C$ 68° C., transition S*$_C$-Ch 94° C., cl.p. (Ch-I) 144.5° C.;

(S)-4-(2-methylbutyloxy)benzoic acid 4-[(trans-4-pentylcyclohexyl)methoxy]phenyl ester, m.p. (C-Ch) 87.5° C., cl.p. (Ch-I) 140.5° C.;

(S)-4-(4-methylhexyloxy)benzoic acid 4-[(trans-4-pentylcyclohexyl)methoxy]phenyl ester, m.p. (C-Ch) 85.5° C., transition S-S*$_C$ 44° C., transition S*$_C$-Ch 85° C., cl.p. (Ch-I) 147.5° C.;

(S)-4-(6-methyloctyloxy)benzoic acid 4-[(trans-4-pentylcyclohexyl)methoxy]phenyl ester, m.p. (C-S*$_C$) 72.5° C., transition S-S*$_C$ 65° C., transition S*$_C$-Ch 107.5° C., cl.p. (Ch-I) 145.5° C.;

(S)-4-(2-methylbutyloxy)benzoic acid 4-[(trans-4-heptylcyclohexyl)methoxy]phenyl ester, m.p. (C-Ch) 66.5° C., transition S-S*$_C$ 63° C., transition S*$_C$-Ch 65° C., cl.p. (Ch-I) 135.5° C.;

(S)-4-(3-methylpentyloxy)benzoic acid 4-[(trans-4-heptylcyclohexyl)methoxy]phenyl ester, (S)-4-(4-methylhexyloxy)benzoic acid 4-[(trans-4-heptylcyclohexyl)methoxy]phenyl ester, m.p. (C-S*$_C$) 77° C., transition S*$_C$-Ch 92.5° C., cl.p. (Ch-I) 142° C.;

(S)-4-(5-methylheptyloxy)benzoic acid 4-[(trans-4-heptylcyclohexyl)methoxy]phenyl ester, (S)-4-(6-methyloctyloxy)benzoic acid 4-[(trans-4-heptylcyclohexyl)methoxy]phenyl ester, m.p. (C-S) 72° C., transition S-S*$_C$ 74° C., transition S*$_C$-Ch 114.5° C., cl.p. (Ch-I) 142° C.;

(S)-4-(2-methylbutyloxy)benzoic acid 4-(trans-4-propylcyclohexyl)phenyl ester, m.p. (C-Ch) 113° C., cl.p. (Ch-I) 168° C.;

(S)-4-(4-methylhexyloxy)benzoic acid 4-(trans-4-propylcyclohexyl)phenyl ester, m.p. (C-Ch) 79.5° C., cl.p. (Ch-I) 169.5° C.;

(S)-4-(6-methyloctyloxy)benzoic acid 4-(trans-4-propylcyclohexyl)phenyl ester, m.p. (C-S*$_C$) 84.5° C., transition S-S*$_C$ 62.5° C.; transition S*$_C$-Ch 86° C., cl.p. (Ch-I) 162.5° C.;

(S)-4-(2-methylbutyloxy)benzoic acid 4-(trans-4-pentylcyclohexyl)phenyl ester, m.p. (C-Ch) 100° C., cl.p. (Ch-I) 161° C.;

(S)-4-(4-methylhexyloxy)benzoic acid 4-(trans-4-pentylcyclohexyl)phenyl ester, m.p. (C-Ch) 85° C., transition S-S*$_C$ 73.5° C., transition S*$_C$-Ch 79.5° C., cl.p. (Ch-I) 165° C.;

(S)-4-(6-methyloctyloxy)benzoic acid 4-(trans-4-pentylcyclohexyl)phenyl ester, m.p. (C-S*$_C$) 75° C., transition S-S*$_C$ 64.5° C., transition S*$_C$-Ch 105.5° C., cl.p. (Ch-I) 162.5° C.;

(S)-4-(4-methylhexyloxy)benzoic acid 4-(trans-4-heptylcyclohexyl)phenyl ester, (S)-4-(6-methyloctyloxy)benzoic acid 4-(trans-4-heptylcyclohexyl)phenyl ester, (S)-4-(4-methylhexyloxy)benzoic acid 2,3-dicyano-4-[2-(trans-4-pentylcyclohexyl)ethyl]phenyl ester, (S)-4-(6-methyloctyloxy)benzoic acid 2,3-dicyano-4-[2-(trans-4-pentylcyclohexyl)ethyl]phenyl ester, m.p. (C-I) 123° C., transition S*$_C$-Ch 113° C., cl.p. (Ch-I) 116° C.;

(S)-4-(6-methyloctyloxy)benzoic acid 2-bromo-4-[2-(trans-4-pentylcyclohexyl)ethyl]phenyl ester m.p. (C-Ch) 57° C., cl.p. (Ch-I) 97° C.;

(S)-4-(2-methylbutoxy)benzoic acid 4-[2-(trans-4-[2-propenyl]cyclohexyl)ethyl]phenyl ester, (S)-4-(4-methylhexyloxy)benzoic acid 4-[2-(trans-4-[2-propenyl]cyclohexyl)ethyl]phenyl ester, (S)-4-(6-methyloctyloxy)benzoic acid 4-[2-(trans-4-[2-propenyl]cyclohexyl)ethyl]phenyl ester, (S)-4-(6-methyloctyloxy)benzoic acid 4-[2-(trans-4-[1E-pentenyl]cyclohexyl)ethyl]phenyl ester, (S)-4-(6-methyloctyloxy)benzoic acid 4-[2-(trans-4-[2Z-pentenyl]cyclohexyl)ethyl]phenyl ester, (S)-4-(6-methyloctyloxy)benzoic acid 4-[2-(trans-4-[3E-pentenyl]cyclohexyl)ethyl]phenyl ester, (S)-4-(6-methyloctyloxy)benzoic acid 4-[2-(trans-4-[4-pentenyl]cyclohexyl)ethyl]phenyl ester, (S)-4-(6-methyloctyloxy)benzoic acid 4-[2-(trans-4-[1E-heptenyl]cyclohexyl)ethyl]phenyl ester, (S)-4-(6-methyloctyloxy)benzoic acid 4-[2-(trans-4-[2Z-heptenyl]cyclohexyl)ethyl]phenyl ester, (S)-4-(6-methyloctyloxy)benzoic acid 4-[2-(trans-4-[3E-heptenyl]cyclohexyl)ethyl]phenyl ester, (S)-4-(6-methyloctyloxy)benzoic acid 4-[2-(trans-4-[4Z-heptenyl]cyclohexyl)ethyl]phenyl ester, (S)-4-(6-methyloctyloxy)benzoic acid 4-[2-(trans-4-[5E-heptenyl]cyclohexyl)ethyl]phenyl ester, (S)-4-(6-methyloctyloxy)benzoic acid 4-[2-(trans-4-[6-heptenyl]cyclohexyl)ethyl]phenyl ester, (S)-4-(6-methyloctyloxy)benzoic acid 4-[2-(trans-4-[1E-pentenyl]cyclohexyl)methoxy]phenyl ester, (S)-4-(6-methyloctyloxy)benzoic acid 4-[2-(trans-4-[2Z-pentenyl]cyclohexyl)methoxy]phenyl ester, (S)-4-(6-methyloctyloxy)benzoic acid 4-[2-(trans-4-[3E-pentenyl]cyclohexyl)methoxy]phenyl ester, (S)-4-(6-methyloctyloxy)benzoic acid 4-[2-(trans-4-[4-pentenyl]cyclohexyl)methoxy]phenyl ester, (S)-4-(6-methyloctyloxy)benzoic acid 4-(trans-4-[1E-pentenyl]cyclohexyl)phenyl ester, (S)-4-(6-methyloctyloxy)benzoic acid 4-(trans-4-[2Z-pentenyl]cyclohexyl)phenyl ester, (S)-4-(6-methyloctyloxy)benzoic acid 4-(trans-4-[3E-pentenyl]cyclohexyl)phenyl ester, (S)-4-(6-methyloctyloxy)benzoic acid 4-(trans-4-[4-pentenyl]cyclohexyl)phenyl ester, 4-hexyloxybenzoic acid 4-[2-(trans-4-propylcyclohexyl)ethyl]phenyl ester, 4-heptyloxybenzoic acid 4-[2-(trans-4-propylcyclohexyl)ethyl]phenyl ester, 4-octyloxybenzoic acid 4-[2-(trans-4-propylcyclohexyl)ethyl]phenyl ester, 4-nonyloxybenzoic acid 4-[2-(trans-4-propylcyclohexyl)ethyl]phenyl ester, 4-decyloxybenzoic acid 4-[2-(trans-4-propylcyclohexyl)ethyl]phenyl ester, 4-undecyloxybenzoic acid 4-[2-(trans-4-propylcyclohexyl)ethyl]phenyl ester, 4-dodecyloxybenzoic acid 4-[2-(trans-4-propylcyclohexyl)ethyl]phenyl ester, 4-hexyloxybenzoic acid 4-[2-(trans-4-pentylcyclohexyl)ethyl]phenyl ester, 4-heptyloxybenzoic acid 4-[2-(trans-4-pentylcyclohexyl)ethyl]phenyl ester, m.p. (C-S$_C$) 67° C., transition S-S$_C$ 51° C., transition S$_C$-N 67.5° C., cl.p. (N-I) 160° C.;

4-octyloxybenzoic acid 4-[2-(trans-4-pentylcyclohexyl)ethyl]phenyl ester, m.p. (C-S$_C$) 68° C., transition S-S$_C$ 57° C., transition S$_C$-N 86.5° C., cl.p. (N-I) 157.5° C.;

4-nonyloxybenzoic acid 4-[2-(trans-4-pentylcyclohexyl)ethyl]phenyl ester, m.p. (C-S$_C$) 61° C., transition S-S$_C$ 57° C., transition S$_C$-N 101° C., cl.p. (N-I) 153.5° C.;

4-decyloxybenzoic acid 4-[2-(trans-4-pentylcyclohexyl)ethyl]phenyl ester, m.p. (C-S$_C$) 60° C., transition S-S$_C$ 57.5° C., transition S$_C$-N 106.5° C., cl.p. (N-I) 152.5° C.;

4-undecyloxybenzoic acid 4-[2-(trans-4-pentylcyclohexyl)ethyl]phenyl ester, 4-dodecyloxybenzoic acid 4-[2-(trans-4-pentylcyclohexyl)ethyl]phenyl ester, m.p. (C-S) 58° C., transition S-S$_C$ 78° C., transition S$_C$-S$_A$ 118° C., transition S$_A$-N 131.5° C., cl.p. (N-I) 147° C.;

4-heptyloxybenzoic acid 4-[2-(trans-4-heptylcyclohexyl)ethyl]phenyl ester, 4-octyloxybenzoic acid 4-[2-(trans-4-heptylcyclohexyl)ethyl]phenyl ester, 4-nonyloxybenzoic acid 4-[2-(trans-4-heptylcyclohexyl)ethyl]phenyl ester, 4-decyloxybenzoic acid 4-[2-(trans-4-heptylcyclohexyl)ethyl]phenyl ester, 4-undecyloxybenzoic acid 4-[2-(trans-4-heptylcyclohexyl)ethyl]phenyl ester, 4-dodecyloxybenzoic acid 4-[2-(trans-4-heptylcyclohexyl)ethyl]phenyl ester, 4-(5-hexenyloxy)benzoic acid 4-[2-(trans-4-propylcyclohexyl)ethyl]phenyl ester, 4-(6-heptenyloxy)benzoic acid 4-[2-(trans-4-propylcyclohexyl)ethyl]phenyl ester, 4-(7-octenyloxy)benzoic acid 4-[2-(trans-4-propylcyclohexyl)ethyl]phenyl ester, 4-(8-nonenyloxy)benzoic acid 4-[2-(trans-4-propylcyclohexyl)ethyl]phenyl ester, 4-(9-decenyloxy)benzoic acid 4-[2-(trans-4-propylcyclohexyl)ethyl]phenyl ester, 4-(10-undecenyloxy)benzoic acid 4-[2-(trans-4-propylcyclohexyl)ethyl]phenyl ester, 4-(11-dodecenyloxy)benzoic acid 4-[2-(trans-4-propylcyclohexyl)ethyl]phenyl ester, 4-(5-hexenyloxy)benzoic acid 4-[2-(trans-4-pentylcyclohexyl)ethyl]phenyl ester, 4-(6-heptenyloxy)benzoic acid 4-[2-(trans-4-pentylcyclohexyl)ethyl]phenyl ester, 4-(7-octenyloxy)benzoic acid 4-[2-(trans-4-pentylcyclohexyl)ethyl]phenyl ester, m.p. (C-S$_C$) 62° C., transition S-S$_C$ 43.5° C., transition S$_C$-N 73° C., cl.p. (N-I) 152.5° C.;

4-(8-nonenyloxy)benzoic acid 4-[2-(trans-4-pentylcyclohexyl)ethyl]phenyl ester, m.p. (C-S$_C$) 55° C., transition S-S$_C$ 44° C., transition S$_C$-N 91.5° C., cl.p. (N-I) 153° C.;

4-(9-decenyloxy)benzoic acid 4-[2-(trans-4-pentylcyclohexyl)ethyl]phenyl ester, m.p. (C-S$_C$) 69° C., transition S-S$_C$ 57° C., transition S$_C$-S$_A$ 104° C., transition S$_A$-N 110° C., cl.p. (N-I) 148° C.;

4-(10-undecenyloxy)benzoic acid 4-[2-(trans-4-pentylcyclohexyl)ethyl]phenyl ester, m.p. (C-S) 51° C., transition S-S$_C$ 69° C., transition S$_C$-S$_A$ 100.5° C., transition S$_A$-N 124° C., cl.p. (N-I) 147.5° C.;

4-(11-dodecenyloxy)benzoic acid 4-[2-(trans-4-pentylcyclohexyl)ethyl]phenyl ester, 4-(5-hexenyloxy)benzoic acid 4-[2-(trans-4-heptylcyclohexyl)ethyl]phenyl ester, 4-(6-heptenyloxy)benzoic acid 4-[2-(trans-4-heptylcyclohexyl)ethyl]phenyl ester, 4-(7-octenyloxy)benzoic acid 4-[2-(trans-4-heptylcyclohexyl)ethyl]phenyl ester, 4-(8-nonenyloxy)benzoic acid 4-[2-(trans-4-heptylcyclohexyl)ethyl]phenyl ester, 4-(9-decenyloxy)benzoic acid 4-[2-(trans-4-heptylcyclohexyl)ethyl]phenyl ester, 4-(10-undecenyloxy)benzoic acid 4-[2-(trans-4-heptylcyclohexyl)ethyl]phenyl ester, 4-(11-dodecenyloxy)benzoic acid 4-[2-(trans-4-heptylcyclohexyl)ethyl]phenyl ester, 4-hexyloxybenzoic acid 2-cyano-4-[2-(trans-4-pentylcyclohexyl)ethyl]phenyl ester, 4-heptyloxybenzoic acid 2-cyano-4-[2-(trans-4-pentylcyclohexyl)ethyl]phenyl ester, 4-octyloxybenzoic acid 2-cyano-4-[2-(trans-4-pentylcyclohexyl)ethyl]phenyl ester, 4-nonyloxybenzoic acid 2-cyano-4-[2-(trans-4-pentylcyclohexyl)ethyl]phenyl ester, 4-decyloxybenzoic acid 2-cyano-4-[2-(trans-4-pentylcyclohexyl)ethyl]phenyl ester, 4-undecyloxybenzoic acid 2-cyano-4-[2-(trans-4-pentylcyclohexyl)ethyl]phenyl ester, 4-dodecyloxybenzoic acid 2-cyano-4-[2-(trans-4-pentylcyclohexyl)ethyl]phenyl ester, m.p. (C-S$_C$) 62° C., transition S$_C$-N 66° C., cl.p. (N-I) 120.5° C.;

4-hexyloxybenzoic acid 2-cyano-4-[2-(trans-4-heptylcyclohexyl)ethyl]phenyl ester, 4-heptyloxybenzoic acid 2-cyano-4-[2-(trans-4-heptylcyclohexyl)ethyl]phenyl ester, 4-octyloxybenzoic acid 2-cyano-4-[2-(trans-4-heptylcyclohexyl)ethyl]phenyl ester, 4-nonyloxybenzoic acid 2-cyano-4-[2-(trans-4-heptylcyclohexyl)ethyl]phenyl ester, 4-decyloxybenzoic acid 2-cyano-4-[2-(trans-4-heptylcyclohexyl)ethyl]phenyl ester, 4-undecyloxybenzoic acid 2-cyano-4-[2-(trans-4-heptylcyclohexyl)ethyl]phenyl ester, 4-dodecyloxybenzoic acid 2-cyano-4-[2-(trans-4-heptylcyclohexyl)ethyl]phenyl ester, 4-octyloxybenzoic acid 4-[(trans-4-pentylcyclohexyl)methoxy]phenyl ester, 4-octyloxybenzoic acid 4-[(trans-4-(1E-pentenyl)cyclohexyl)methoxy]phenyl ester, 4-octyloxybenzoic acid 4-[(trans-4-(4-pentenyl)cyclohexyl)methoxy]phenyl ester, 4-(7-octenyloxy)benzoic acid 4-[(trans-4-pentylcyclohexyl)methoxy]phenyl ester, 4-(8-nonenyloxy)benzoic acid 4-[(trans-4-pentylcyclohexyl)methoxy]phenyl ester, 4-(9-decenyloxy)benzoic acid 4-[(trans-4-pentylcyclohexyl)methoxy]phenyl ester, (S)-4-(6-methyloctyloxy)benzoic acid 4-[trans-4-(1E-pentenyl)cyclohexyl]phenyl ester, (S)-4-(6-methyloctyloxy)benzoic acid 4-[trans-4-(4-pentenyl)cyclohexyl]phenyl ester, 4-octyloxybenzoic acid 4-[trans-4-(1E-pentenyl)cyclohexyl]phenyl ester, 4-octyloxybenzoic acid 4-[trans-4-(4E-pentenyl)cyclohexyl]phenyl ester, 4-(7-octenyloxy)benzoic acid 4-[trans-4-pentylcyclohexyl]phenyl ester, 4-(8-nonenyloxy)benzoic acid 4-[trans-4-pentylcyclohexyl]phenyl ester, 4-(9-decenyloxy)benzoic acid 4-[trans-4-pentylcyclohexyl]phenyl ester,
4-(5-hexenyloxy)benzoic acid 2-cyano-4-[2-(trans-4-pentylcyclohexyl)ethyl]phenyl ester,
4-(6-heptenyloxy)benzoic acid 2-cyano-4-[2-(trans-4-pentylcyclohexyl)ethyl]phenyl ester,
4-(7-octenyloxy)benzoic acid 2-cyano-4-[2-(trans-4-pentylcyclohexyl)ethyl]phenyl ester,
4-(8-nonenyloxy)benzoic acid 2-cyano-4-[2-(trans-4-pentylcyclohexyl)ethyl]phenyl ester,
4-(9-decenyloxy)benzoic acid 2-cyano-4-[2-(trans-4-pentylcyclohexyl)ethyl]phenyl ester,
4-(10-undecenyloxy)benzoic acid 2-cyano-4-[2-(trans-4-pentylcyclohexyl)ethyl]phenyl ester,
4-(11-dodecenyloxy)benzoic acid 2-cyano-4-[2-(trans-4-pentylcyclohexyl)ethyl]phenyl ester.

EXAMPLE 6

A mixture of 2 g of (S)-4-(6-methyloctyloxy)benzoic acid 2-bromo-4-[2-(trans-4-pentylcyclohexyl)ethyl]phenyl ester, 0.5 g of anhydrous copper(I) cyanide and 50 ml of absolute 1-methyl-2-pyrrolidone was heated to 185° C. on a oil-bath for 2 hours. The cooled mixture was subsequently treated with 50 ml of 15% ammonia solution and stirred for 30 minutes. Thereafter, the reaction mixture was extracted three times with 50 ml of diethyl ether each time. The combined organic phases were washed twice with 250 ml of water each time, dried over magnesium sulphate and concentrated. Chromatography of the residue on silica gel with toluene/hexane (vol. 1:1) gave 0.1 g of (S)-4-(6-methyloctyloxy)benzoic acid 2-cyano-4-[2-(trans-4-pentylcyclohexyl)ethyl]phenyl ester; m.p. (C-Ch) 80° C., transition S*$_C$-Ch 50° C. (monotropic), cl.p. (Ch-I) 120° C.

EXAMPLE 7

2.5 g of (S)-4-(6-methyloctyloxy)benzoic acid were heated to 80° C. for 1 hour with 25 ml of thionyl chloride in toluene. The solution obtained was evaporated under reduced pressure, the residue was treated with 20 ml of absolute toluene and the solution was again evaporated under reduced pressure. The acid chloride obtained was taken up in 50 ml of absolute toluene and treated with a solution of 1.1 g of hydroquinone in 10 ml of absolute pyridine. The reaction mixture was heated to reflux for 1 hour, then cooled, treated with dilute hydrochloric acid and extracted three times with 50 ml of dichloromethane each time. The combined organic phases were washed twice with 250 ml of water each time, dried over magnesium sulphate and concentrated. The crude product obtained was purified by column chromatography on silica gel with toluene/ethyl acetate (vol. 4:1). Recrystallization of the resulting product from ethanol gave 2.0 g of (S)-4-(6-methyloctyloxy)benzoic acid 4-hydroxyphenyl ester of m.p. 75° C.

EXAMPLE 8

2.0 g of (S)-4-(6-methyloctyloxy)benzoic acid 4-hydroxyphenyl ester, 1.1 g of trans-4-pentylcyclohexanecarboxylic acid and 0.1 g of 4-(dimethylamino)pyridine were dissolved in 50 ml of dichloromethane and the solution was treated portionwise in 10 minutes while stirring with 1.4 g of N,N'-dicyclohexylcarbodiimide. The mixture was stirred at room temperature overnight and then filtered. The filtrate was diluted with dichloromethane, washed twice with 50 ml of saturated sodium bicarbonate solution each time and then washed with water, dried over sodium sulphate and concentrated. The crude product obtained was purified by chromatography on silica gel with toluene. The resulting (S)-4-(6-methyloctyloxy)benzoic acid 4-(trans-4-pentylcyclohexylcarbonyloxy)phenyl ester was recrystallized from methanol and ethanol; m.p. (C-S) 66° C., transition S-S*$_C$ 80° C., transition S*$_C$-Ch 112° C., cl.p. (Ch-I) 186° C.

The following compounds can be prepared in an analogous manner:

(S)-4-(2-Methylbutyloxy)benzoic acid 4-(trans-4-pentylcyclohexylcarbonyloxy)phenyl ester,
(S)-4-(4-methylhexyloxy)benzoic acid 4-(trans-4-pentylcyclohexylcarbonyloxy)phenyl ester,
(S)-4-(2-methylbutyl)benzoic acid 4-(trans-4-pentylcyclohexylcarbonyloxy)phenyl ester,
(S)-4-(4-methylhexyl)benzoic acid 4-(trans-4-pentylcyclohexylcarbonyloxy)phenyl ester,
(S)-4-(6-methyloctyl)benzoic acid 4-(trans-4-pentylcyclohexylcarbonyloxy)phenyl ester,
(S)-4-(6-methyloctyloxy)benzoic acid 4-[trans-4-(1E-pentenyl)cyclohexylcarbonyloxy]phenyl ester,
(S)-4-(6-methyloctyloxy)benzoic acid 4-[trans-4-(4-pentenyl)cyclohexylcarbonyloxy]phenyl ester,
(S)-4-(6-methyloctyloxy)benzoic acid 4-[trans-4-(5-hexenyl)cyclohexylcarbonyloxy]phenyl ester,
(S)-4-(6-methyloctyloxy)benzoic acid 4-[trans-4-(6-heptenyl)cyclohexylcarbonyloxy]phenyl ester,
4-hexyloxybenzoic acid 4-(trans-4-pentylcyclohexylcarbonyloxy)phenyl ester,
4-heptyloxybenzoic acid 4-(trans-4-pentylcyclohexylcarbonyloxy)phenyl ester,
4-octyloxybenzoic acid 4-(trans-4-pentylcyclohexylcarbonyloxy)phenyl ester,
4-nonyloxybenzoic acid 4-(trans-4-pentylcyclohexylcarbonyloxy)phenyl ester,
4-decyloxybenzoic acid 4-(trans-4-pentylcyclohexylcarbonyloxy)phenyl ester,
4-(5-hexenyloxy)benzoic acid 4-(trans-4-pentylcyclohexylcarbonyloxy)phenyl ester,
4-(6-heptenyloxy)benzoic acid 4-(trans-4-pentylcyclohexylcarbonyloxy)phenyl ester,
4-(7-octenyloxy)benzoic acid 4-(trans-4-pentylcyclohexylcarbonyloxy)phenyl ester,
4-(8-nonenyloxy)benzoic acid 4-(trans-4-pentylcyclohexylcarbonyloxy)phenyl ester,
4-(9-decenyloxy)benzoic acid 4-(trans-4-pentylcyclohexylcarbonyloxy)phenyl ester,
4-octyloxybenzoic acid 4-[trans-4-(1E-pentenyl)cyclohexylcarbonyloxy]phenyl ester,
4-octyloxybenzoic acid 4-[trans-4-(4-pentenyl)cyclohexylcarbonyloxy]phenyl ester,
4-octyloxybenzoic acid 4-[trans-4-(5-hexenyl)cyclohexylcarbonyloxy]phenyl ester,
4-octyloxybenzoic acid 4-[trans-4-(6-heptenyl)cyclohexylcarbonyloxy]phenyl ester,
(S)-4-(4-methylhexyloxy)benzoic acid 4-(trans-4-pentylcyclohexyloxycarbonyl)phenyl ester,
(S)-4-(6-methyloctyloxy)benzoic acid 4-(trans-4-pentylcyclohexyloxycarbonyl)phenyl ester,
(S)-4-(6-methyloctyloxy)benzoic acid 4-[trans-4-(1E-pentenyl)cyclohexyloxycarbonyl)phenyl ester,
(S)-4-(6-methyloctyloxy)benzoic acid 4-[trans-4-(4-pentenyl)cyclohexyloxycarbonyl)phenyl ester,
(S)-4-(6-methyloctyloxy)benzoic acid 4-[trans-4-(5-hexenyl)cyclohexyloxycarbonyl)phenyl ester,
4-(7-octenyloxy)benzoic acid 4-(trans-4-pentylcyclohexyloxycarbonyl)phenyl ester, 4-(8-nonenyloxy)benzoic acid 4-(trans-4-pentylcyclohexyloxycarbonyl)phenyl ester,
4-(9-decenyloxy)benzoic acid 4-(trans-4-pentylcyclohexyloxycarbonyl)phenyl ester,
4-octyloxybenzoic acid 4-[trans-4-(1E-pentenyl)cyclohexyloxycarbonyl)phenyl ester,
4-octyloxybenzoic acid 4-[trans-4-(4-pentenyl)cyclohexyloxycarbonyl)phenyl ester,
4-octyloxybenzoic acid 4-[trans-4-(5-hexenyl)cyclohexyloxycarbonyl)phenyl ester.

MIXTURE EXAMPLE A 27.2 wt. % of 4-dodecyloxybenzoic acid 4-[2-(trans-4-pentylcyclohexyl)ethyl]phenyl ester,
23.6 wt. % of 4-(10-undecenyloxy)benzoic acid 4-[2-(trans-4-pentylcyclohexyl)ethyl]phenyl ester,
17.0 wt. % of 5-decyl-2-(4-hexyloxyphenyl)pyrimidine,
17.0 wt. % of 5-decyl-2-(4-octyloxyphenyl)pyrimidine,
15.2 wt. % of 5-decyl-2-(4-decyloxyphenyl)pyrimidine.

Cl.p. (N-I) 100° C., transition $N$-$S_A$ 80° C., transition $S_A$-$S_C$ 69° C. The $S_C$ phase did not crystallize upon cooling to $-2°$ C.

MIXTURE EXAMPLE B 55 wt. % of (S)-4-(6-methyloctyloxy)benzoic acid 4-[2-(trans-4-pentylcyclohexyl)ethyl]phenyl ester,
45 wt. % of (S)-4-decyloxybenzoic acid 4-(2-methylbutyloxy)phenyl ester.

Cl. p. (Ch-I) 96.5° C., transition Ch-$S^*_C$ 64° C., transition $S^*_C$-S 27° C.

MIXTURE EXAMPLE C 50 wt. % of 4-nonyloxybenzoic acid 4-[2-(trans-4-pentylcyclohexyl)ethyl]phenyl ester,
50 wt. % 4-dodecyloxybenzoic acid 2-cyano-4-[2-(trans-4-pentylcyclohexyl)ethyl]phenyl ester.

Cl. p. (N-I) 134° C., transition N-$S_C$ 68° C., m.p. (C-$S_C$) 46° C.

We claim:
1. A compound of the formula

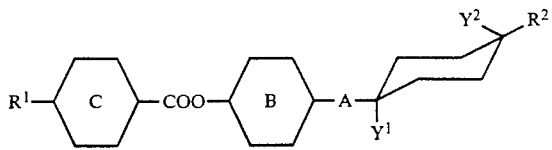

wherein A is $-CH_2CH_2$; rings B and C each are 1,4-phenylene which is unsubstituted or substituted with cyano or halogen; $Y^1$ and $Y^2$ are hydrogen; $R^1$ is straight-chain $C_{4-18}$-alkoxy; and $R^2$ is straight-chain $C_{3-18}$-alkyl.

2. A liquid crystalline mixture with at least two components, wherein at least one of those components is a compound of the formula

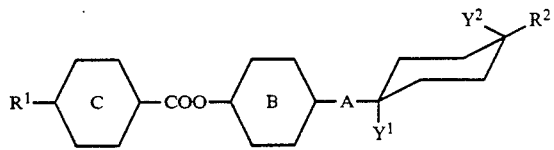

wherein A is $-CH_2CH_2$; rings B and C each are 1,4-phenylene which is unsubstituted or substituted with cyano or halogen; $Y^1$ and $Y^2$ are hydrogen; $R^1$ is straight-chain $C_{4-18}$-alkoxy; and $R^2$ is straight-chain $C_{3-18}$-alkyl.

3. A compound according to claim 1, wherein $Y^1$ and $Y^2$ are hydrogen and ring C is 1,4-phenylene.

4. A compound according to claim 1, wherein ring B is 1,4-phenylene, 2-cyano-1,4-phenylene, 2,3-dicyano-1,4-phenylene, 2-halogeno-1,4-phenylene or 2,3-dihalogeno-1,4-phenylene.

5. A compound according to claim 1, wherein $R^1$ and $R^2$ together have at least 7 carbon atoms.

* * * * *